US012257426B2

(12) United States Patent
Boelke et al.

(10) Patent No.: US 12,257,426 B2
(45) Date of Patent: Mar. 25, 2025

(54) COMPRESSIBLE ROTOR

(71) Applicant: Abiomed Europe GmbH, Aachen (DE)

(72) Inventors: Tino Andreas Boelke, Aachen (DE);
Gerd Bruno Spanier, Aachen (DE);
Claudia Mourran, Aachen (DE);
Smriti Singh, Aachen (DE)

(73) Assignee: ABIOMED EUROPE GMBH, Aachen (DE)

( * ) Notice: Subject to any disclaimer, the term of this patent is extended or adjusted under 35 U.S.C. 154(b) by 0 days.

(21) Appl. No.: 18/519,584

(22) Filed: Nov. 27, 2023

(65) Prior Publication Data

US 2024/0198083 A1  Jun. 20, 2024

Related U.S. Application Data

(60) Provisional application No. 63/470,663, filed on Jun. 2, 2023, provisional application No. 63/429,649, filed on Dec. 2, 2022.

(51) Int. Cl.
| | |
|---|---|
| *A61M 60/808* | (2021.01) |
| *B29C 45/00* | (2006.01) |
| *F04D 29/02* | (2006.01) |
| *F04D 29/18* | (2006.01) |
| *B29K 67/00* | (2006.01) |

(Continued)

(52) U.S. Cl.
CPC ....... *A61M 60/808* (2021.01); *B29C 45/0001* (2013.01); *F04D 29/026* (2013.01); *F04D 29/181* (2013.01); *B29K 2067/00* (2013.01); *B29K 2083/00* (2013.01); *B29K 2995/0088* (2013.01); *B29L 2031/08* (2013.01)

(58) Field of Classification Search
CPC .............. A61M 60/804; A61M 60/806; A61M 60/808; A61M 60/81; A61M 60/812; F04D 29/18; F04D 29/181
See application file for complete search history.

(56) References Cited

U.S. PATENT DOCUMENTS

| 9,611,743 B2 * | 4/2017 | Toellner ................ A61M 60/13 |
| 10,215,187 B2 * | 2/2019 | McBride ............... F04D 29/026 |

(Continued)

FOREIGN PATENT DOCUMENTS

| WO | WO-2018139508 A1 * | 8/2018 | ............ A61M 60/00 |

*Primary Examiner* — David E Sosnowski
*Assistant Examiner* — Maxime M Adjagbe
(74) *Attorney, Agent, or Firm* — MEAGHER EMANUEL LAKS GOLDBERG & LIAO, LLP

(57) ABSTRACT

A rotor for a pump, such as a blood pump, may include a hub configured to rotate around a central axis, and at least one rotor blade coupled to and extending away from an outer surface of the hub, the rotor blade comprising a medical-grade polyurethane, the rotor blade configured to have a crimped state and a running state. The medical-grade polyurethane may be configured for casting or injection molding, and upon curing, the medical-grade material advantageously has a shore A hardness of 90-100, or a shore B hardness of 35-55, and a Young's modulus of 60 MPa-250 MPa. When crimped, the rotor blades are compressed and exposed to strains of up to about 160% in a dry environment at temperatures of 20-25° C. When running, the rotor blades are expanded and exposed to strains of up to 10% in a wet environment at temperatures of 36-38° C.

20 Claims, 9 Drawing Sheets

(51) Int. Cl.
    *B29K 83/00*    (2006.01)
    *B29L 31/08*    (2006.01)

(56) References Cited

U.S. PATENT DOCUMENTS

| | | | |
|---|---|---|---|
| 2012/0142994 A1* | 6/2012 | Toellner | F04D 15/0055 |
| | | | 219/121.72 |
| 2013/0177409 A1* | 7/2013 | Schumacher | A61M 60/808 |
| | | | 416/131 |
| 2021/0236797 A1* | 8/2021 | D'Ambrosio | A61M 60/237 |
| 2022/0288381 A1* | 9/2022 | Siess | A61M 60/174 |

* cited by examiner

COMPRESSIBLE ROTOR

CROSS-REFERENCE TO RELATED APPLICATIONS

The present application claims priority to U.S. Provisional Patent Application Nos. 63/429,649, filed Dec. 2, 2022, and 63/470,663, filed Jun. 2, 2023, the contents of each being incorporated by reference herein in its entirety.

TECHNICAL FIELD

The present disclosure is drawn to rotors for moving bodily fluids, and specifically compressible rotors for moving blood.

BACKGROUND

Medical pumps, and particularly blood pumps, require very specific design and performance characteristics to be met. To provide the necessary flow of fluids at a manageable rotation speed, pump rotors must have blades with certain minimum outer diameters, larger than most blood vessel inner diameters. To improve the ease of surgical insertion, and to ensure the rotor will have minimal impact as it is surgically inserted into and through small blood vessels, the rotor blades must be compressible. However, to achieve such properties, medical grade polymers with a very defined set of mechanical properties are required. To date, the combination of both desired requirements (e.g., (1) medical-grade materials and (2) defined mechanical properties) could not be achieved for the manufacturing of such rotors. The use of a non-medical grade polymer is potentially problematic when used inside a patient for extended periods, such as for blood pumps used to alleviate certain heart-related conditions. Therefore, a compressible rotor that can be manufactured via conventional manufacturing techniques from medical-grade polymers is desirable and useful.

BRIEF SUMMARY

Various deficiencies in the prior art are addressed below by the disclosed system and method.

A rotor may be provided. Advantageously, the rotor may include a hub configured to rotate around a central axis. The rotor may include at least one rotor blade coupled to the hub and extending away from an outer surface of the hub. The rotor blade(s) include a medical-grade material. The rotor blade(s) may be configured to have a crimped state and a running state.

The medical-grade material, such as a medical-grade thermoplastic polyurethane (TPU), or other thermoplastic elastomer (TPE), such as polyvinyl acetate, or a blend/combination thereof, may be configured for casting or injection molding, and upon curing, the medical-grade material advantageously has a shore A hardness value of 90-100, or a shore B hardness value of 35-55, as determined using DIN ISO 7619-1 and a Young's modulus of 60 MPa-250 MPa determined using ISO 527. In the crimped state, the rotor blade(s) may be compressed and exposed to strains of up to about 160% in a dry environment at temperatures of 20-25° C. In the running state, the rotor blade(s) may be expanded and exposed to strains of up to 10% in a wet environment (e.g., exposed to blood) at temperatures of 36-42° C., such as 36-38° C.

In some embodiments, the medical-grade material may have a tensile strength of 15 MPa-25 MPa, and an elongation at break of 500%-600% as determined using DIN 53504. In some embodiments, the medical-grade material may be selected such that a stress of the medical-grade material at 5% strain, a stress at 10% strain, a stress at 20% strain, and a stress at 50% strain have a range of no more than 0.5 MPa, as determined using DIN 53504. In some embodiments, the medical-grade material may have a storage modulus exhibiting a rubbery plateau at temperatures from no more than 0° C. to no less than 150° C. In some embodiments, the medical-grade material may have a storage modulus of 50-100 MPa at 0° C.

In some embodiments, the medical-grade material may be a biocompatible material. In some embodiments, the medical-grade material may be a thermoplastic polyurethane, a polyvinyl acetate, or a blend. In some embodiments, the medical-grade material may be a single-component resin. In some embodiments, the medical-grade material may be a resin having a first component and a second component. The first component may be a prepolymer of: (i) hexamethyl diisocyanate (HDI), methylene dicyclohexyl diisocyanate (H12MDI), and/or methylene diphenyl diisocyanate (MDI); (ii) polytetramethylene ether glycol (PTMEG) with a molecular weight of 500 g/mol-6,000 g/mol, or polypropylene glycol (PPG); and (iii) optionally, polyesters like poly (caprolactone), polyethylene adipate, or polybutylene adipate, where the first component may have an average molecular weight of 10,000 g/mol-14,000 g/mol. The second component may be diethyltoluenediamine (DETDA) or 1,4 butane diol. In some embodiments, the first component and second component may be present at a stoichiometric ratio. In some embodiments, the first component and second component may be present at a non-stoichiometric ratio. In some embodiments, the medical-grade material may include a catalyst and/or an inhibitor.

In some embodiments, the medical-grade material may be a resin having one or more soft segments and one or more hard segments. The one or more soft segments may include a di- or tri-functionally terminated telechelic soft segment oligomer, and the one or more hard segments may include a diisocyanate. The medical-grade material may also include one or more chain extenders.

In some embodiments, the medical-grade material may be a silicone-polycarbonate-urethane. The silicone-polycarbonate-urethane may include polydimethylsiloxane (PDMS), and/or may include one or more chain extenders.

In some embodiments, the medical-grade material may include one or more additional components, which may be added to accommodate for, e.g., material variations, or to achieve a desired reactivity, curing speed, mold viscosity, surface tension, etc.

In some embodiments, the rotor may be formed by die-casting or injection molding. In some embodiments, the rotor may be formed by vacuum-casting or vacuum-socketing.

In some embodiments, the medical-grade material may be selected such that a force-elongation profile of the medical-grade material exhibits a region with a first slope below a deformation threshold and a plateau region above the deformation threshold. In some embodiments, values of force in the plateau region may be 9-11 N.

In some embodiments, the medical-grade material may be configured to survive elongations greater than 100% without rupturing. In some embodiments, the medical-grade material may be configured such that, when exposed to an elongation of 100% for at least 15 minutes, the material exhibits less than 5% non-recoverable plastic deformation. In some embodiments, the medical-grade material may be sterilizable. In some embodiments, the medical-grade material may be ethylene oxide sterilizable. In some embodiments, the medical-grade material may be selected such that a dimensional molding shrinkage is less than 1% upon cooling to room temperature after forming the rotor.

In some embodiments, the at least one blade may have a substantially smooth exterior surface. In some embodiments, the at least one blade may have an exterior surface that is substantially free of an orange peel effect. In some embodiments, the at least one blade may have an axial length of 7-8 mm. In some embodiments, the at least one blade may have an outer diameter of 5-6 mm in the running state. In some embodiments, the at least one rotor blade may be helically wound around the hub. In some embodiments, the at least one rotor blade may have a constant helical pitch. In some embodiments, a helical pitch of the at least one rotor blade may vary along a length of the hub. In some embodiments, the at least one rotor blade may include a concave side and a convex side. In some embodiments, the concave side may be laid against an exterior surface of the hub when in the crimped state.

In some embodiments, the hub may have an axial length of 9-11 mm. In some embodiments, the hub may be free of a lumen extending from a distal end to a proximal end. In some embodiments, the hub may have a lumen extending from a distal end to a proximal end. In some embodiments, the hub and the at least one rotor blade are cast or molded, and particularly may be injection molded, from the medical-grade material.

In some embodiments, a rotor may be provided that includes a hub configured to rotate around a central axis, and at least one rotor blade coupled to the hub and extending away from an outer surface of the hub, where the rotor blade may include a medical-grade polyurethane or other thermoplastic elastomer, where the rotor blade may have a crimped state and a running state.

In some embodiments, the medical-grade polyurethane may be a resin having a first component and a second component. The first component may be a prepolymer including: (i) hexamethyl diisocyanate (HDI), methylene dicyclohexyl diisocyanate (H12MDI), and/or methylene diphenyl diisocyanate (MDI); (ii) polytetramethylene ether glycol (PTMEG, sometimes referred to as polytetrahydrofuran) with a molecular weight of 500 g/mol-6,000 g/mol, or polypropylene glycol (PPG); and (iii) optionally, polyesters like poly(caprolactone), polyethylene adipate, or polybutylene adipate, where the first component may have an average molecular weight of 10,000 g/mol-14,000 g/mol. The second component may be diethyltoluenediamine (DETDA) or 1,4 butane diol. In some embodiments, the first component and second component may be present at a stoichiometric ratio. In some embodiments, the first component and second component may be present at a non-stoichiometric ratio. In some embodiments, the medical-grade polyurethane may include a catalyst and/or an inhibitor.

In some embodiments, the first component comprises HDI, PPG, and poly(caprolactone), and the second component is DETDA. In some embodiments, the first component comprises H12MDI, PPO, and poly(caprolactone), and the second component is DETDA. In some embodiments, the first component comprises H12MDI and/or MDI, PPO, and PTMEG, and the second component is 1,4 butane diol.

In some embodiments, the medical-grade polyurethane or other thermoplastic elastomer may be a resin having one or more soft segments and one or more hard segments. The one or more soft segments may include a di- or tri-functionally terminated telechelic soft segment oligomer, and the one or more hard segments may include a diisocyanate.

The medical-grade polyurethane or other thermoplastic elastomer may also include one or more chain extenders.

In some embodiments, the medical-grade polyurethane or other thermoplastic elastomer may be a silicone-polycarbonate-urethane. The silicone-polycarbonate-urethane may include polydimethylsiloxane (PDMS), and/or may include one or more chain extenders.

In some embodiments, the at least one blade may have a substantially smooth exterior surface. In some embodiments, the at least one blade may have an exterior surface that is substantially free of an orange peel effect. In some embodiments, the at least one blade may have an axial length of 7-8 mm. In some embodiments, the at least one blade may have an outer diameter of 5-6 mm in the running state. In some embodiments, the at least one rotor blade may be helically wound around the hub. In some embodiments, the at least one rotor blade may have a constant helical pitch. In some embodiments, a helical pitch of the at least one rotor blade may vary along a length of the hub. In some embodiments, the at least one rotor blade may include a concave side and a convex side. In some embodiments, the concave side may be laid against an exterior surface of the hub when in the crimped state.

In some embodiments, the hub may have an axial length of 9-11 mm. In some embodiments, the hub may be free of a lumen extending from a distal end to a proximal end. In some embodiments, the hub may have a lumen extending from a distal end to a proximal end. In some embodiments, the hub and the at least one rotor blade are cast or molded, and particularly may be injection molded, from the medical-grade material.

In some embodiments, a pump may be provided. The pump may include a pump housing that is expandable and compressible. The pump may include a rotor as disclosed herein, the rotor being disposed in the pump housing.

In some embodiments, the pump may include a drive shaft operably coupled to the rotor. In some embodiments, the drive shaft may be a metallic drive shaft. In some embodiments, the rotor may be adhered to the metallic drive shaft. In some embodiments, the metallic drive shaft may include at least one structure extending radially outward from a central axis of the drive shaft, the at least on structure configured to interact with the rotor. In some embodiments, the metallic drive shaft may be free of structures extending radially outward from the drive shaft that interact with the rotor. In some embodiments, the metallic drive shaft may have been surface treated.

In some embodiments, the pump may include a motor operably coupled to a proximal end of the drive shaft. In some embodiments, the pump may include a catheter having a proximal end and a distal end, the distal end operably coupled to a proximal end of the pump housing. In some embodiments, the drive shaft may be disposed in a lumen extending from the proximal end to the distal end of the catheter. In some embodiments, the pump housing may be configured to be inserted into a blood vessel of a patient. In some embodiments, the pump housing may be configured to be inserted into a ventricle of a heart of a patient.

In some embodiments, a system may be provided. The system may include a pump as disclosed herein. A controller may be operably coupled to the pump.

In some embodiments, a kit may be provided. The kit may include a pump as disclosed herein, and a controller that may be configured to be operably coupled to the pump.

BRIEF DESCRIPTION OF DRAWINGS

The accompanying drawings, which are incorporated in and constitute a part of this specification, illustrate embodiments of the present invention and, together with a general description of the invention given above, and the detailed description of the embodiments given below, serve to explain the principles of the present invention.

Figure 1:
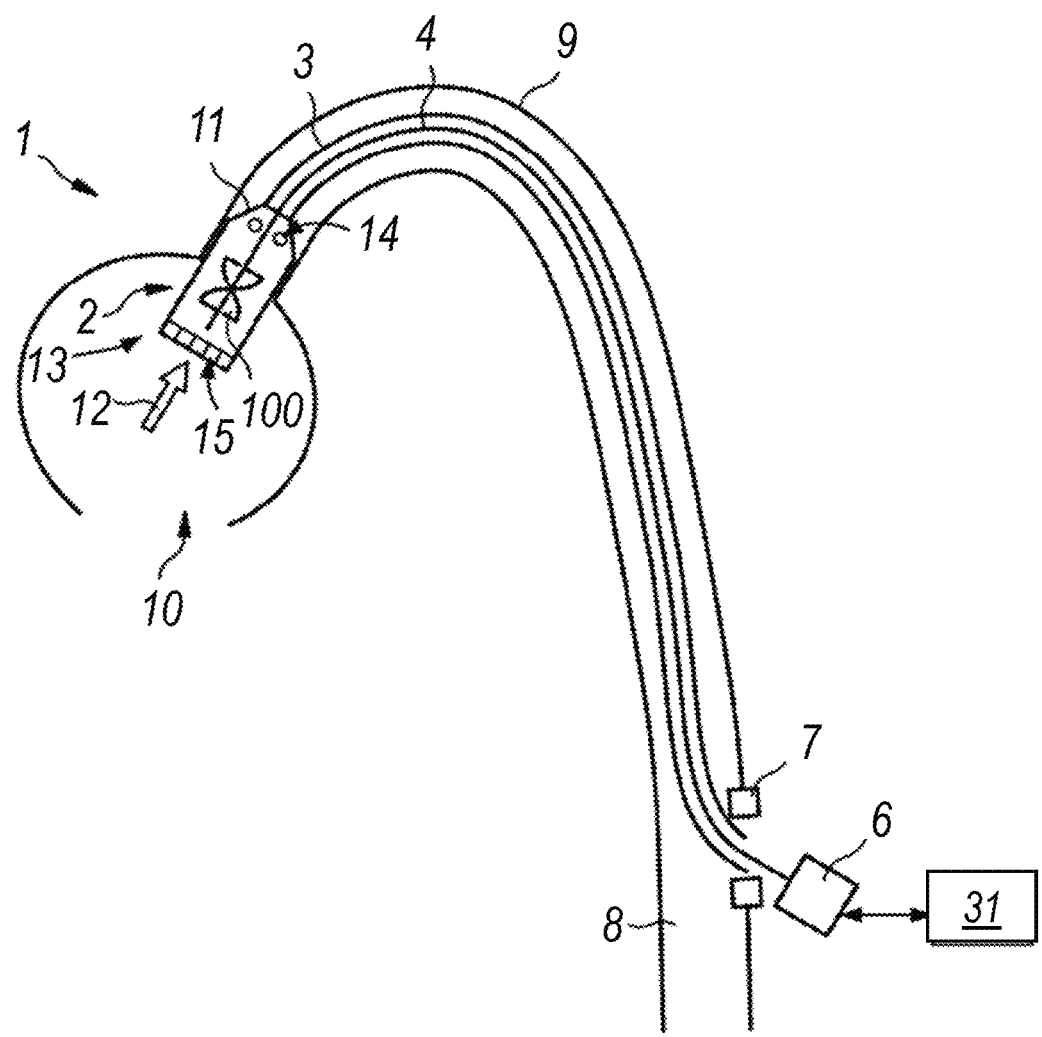
FIG. 1 is a schematic illustration of a system including a pump with a rotor inserted into a blood vessel of a patient.

It should be understood that the appended drawings are not necessarily to scale, presenting a somewhat simplified representation of various features illustrative of the basic principles of the invention. The specific design features of the sequence of operations as disclosed herein, including, for example, specific dimensions, orientations, locations, and shapes of various illustrated components, will be determined in part by the particular intended application and use environment. Certain features of the illustrated embodiments have been enlarged or distorted relative to others to facilitate visualization and clear understanding. In particular, thin features may be thickened, for example, for clarity or illustration.

DETAILED DESCRIPTION

The following description and drawings merely illustrate the principles of the invention. It will thus be appreciated that those skilled in the art will be able to devise various arrangements that, although not explicitly described or shown herein, embody the principles of the invention and are included within its scope. Furthermore, all examples recited herein are principally intended expressly to be only for illustrative purposes to aid the reader in understanding the principles of the invention and the concepts contributed by the inventor(s) to furthering the art and are to be construed as being without limitation to such specifically recited examples and conditions. Additionally, the term, "or," as used herein, refers to a non-exclusive or, unless otherwise indicated (e.g., "or else" or "or in the alternative"). Also, the various embodiments described herein are not necessarily mutually exclusive, as some embodiments can be combined with one or more other embodiments to form new embodiments.

The numerous innovative teachings of the present application will be described with particular reference to the presently preferred exemplary embodiments. However, it should be understood that this class of embodiments provides only a few examples of the many advantageous uses of the innovative teachings herein. In general, statements made in the specification of the present application do not necessarily limit any of the various claimed inventions. Moreover, some statements may apply to some inventive features but not to others. Those skilled in the art and informed by the teachings herein will realize that the invention is also applicable to various other technical areas or embodiments, such as seismology and data fusion.

Various embodiments are directed to pumps, and blood pumps in particular, with collapsible rotors made from medical-grade polymers.

The term "medical-grade" material as used herein refers to materials intended for use in a finished medical device product, such as a product in accordance to medical device regulation EU2017/745 of the European Parliament and Council of Medical Devices (MDR) and Committee for Medicinal Products for Human Use (CHMP). Such medical grade materials should comply with numerous minimum requirements, including requiring rigorous change management procedures with regards to potential planned changes in the material specification or composition, manufacturing site, manufacturing technology, or changes in regulatory status, specific quality management regarding the development and handling of such materials, guarantees on security or supply and availability, and support for satisfying regulatory testing requirements. Such regulatory testing requirements includes tests relating to biological requirements, such as biocompatibility tests according to DIN EN ISO 10933 standards and/or US Pharmacopoeia (USP) class VI, permissible limits of various chemical components, including metal ions, and tests relating to sterilization of the product (such as resistance to radiation, ethylene oxide, or steam sterilization as appropriate). In many cases, a medical grade material may be one for which a drug master file (DMF) has been created and filed with the regulatory authority (such as the Food and Drug Administration (FDA) in the United States), and is being maintained.

FIG. 1 shows a schematic overview of a rotor used in a pump. The pump 1 may include a pump housing 2 and a catheter 3 having a lumen therethrough. Pump housing 2 may include proximal end 11 and distal end 13. In some embodiments, the distal end 13 may include one or more openings 15 forming an inlet for drawing blood into pump housing 2. In one aspect, openings 15 may form an inflow cage. The direction of the inflowing blood is symbolized by the arrow 12. Proximal end 11 may include one or more openings 14 forming an outlet for conveying the blood drawn in by the inlet into a blood vessel of a patient.

A drive shaft 4 may be arranged in the lumen of catheter 3. The proximal end of drive shaft 4 may be attached to a motor 6 and a distal portion of the drive shaft may extend into the interior of pump housing 2. A rotor 100 may be mounted to the distal portion of drive shaft 4 and arranged in pump housing 2. Motor 6 may rotate the drive shaft 4, which may rotate rotor 100. It is to be appreciated that drive shaft 4 may be flexible to enable deployment of drive shaft 4 and catheter 3 into the patient.

As illustrated in FIG. 1, the pump 1 may be introduced into a blood vessel of a patient via a port 7. For example, pump 1 may be introduced and provided through an arteriotomy in femoral artery 8 and passed through aortic arch 9 and into a heart ventricle 10 of the patient, such that pump housing 2 lies in the region of the aortic valve (not shown). It is to be appreciated that distal end 13 of pump housing 2 may extend into a left ventricle of the patient and proximal end 11 is disposed in the aorta of the patient. Rotor 100 may be rotated by drive shaft 4 and motor 6 at a speed between, e.g., 3,000 and 50,000 rpm (revolutions per minute) for conveying blood from heart ventricle 10 into the openings 15 of the inlet at distal end 13 of pump housing (as indicated by arrow 12) and out of the openings 14 of the outlet at proximal end 11 into the aorta.

In one aspect, pump 1 may include a controller 31 that is operably coupled to pump 1, and that is configured for controlling and driving motor 6 to control the operation of pump 1. The controller may be integrated in motor 6 or be separately located from motor 6.

In one aspect, pump housing 2 and rotor 100 may be configured to be radially compressible to a compressed (or "crimped") state to enable efficient deployment of pump 1 through the blood vessel of the patient. Moreover, after the placement of pump housing 2 and rotor 100 in and/or proximately to the ventricle 10 of the patient, pump housing 2 and rotor 100 may be configured to be radially expandable to an expanded (or "running") state for normal operation.

Figure 2A:
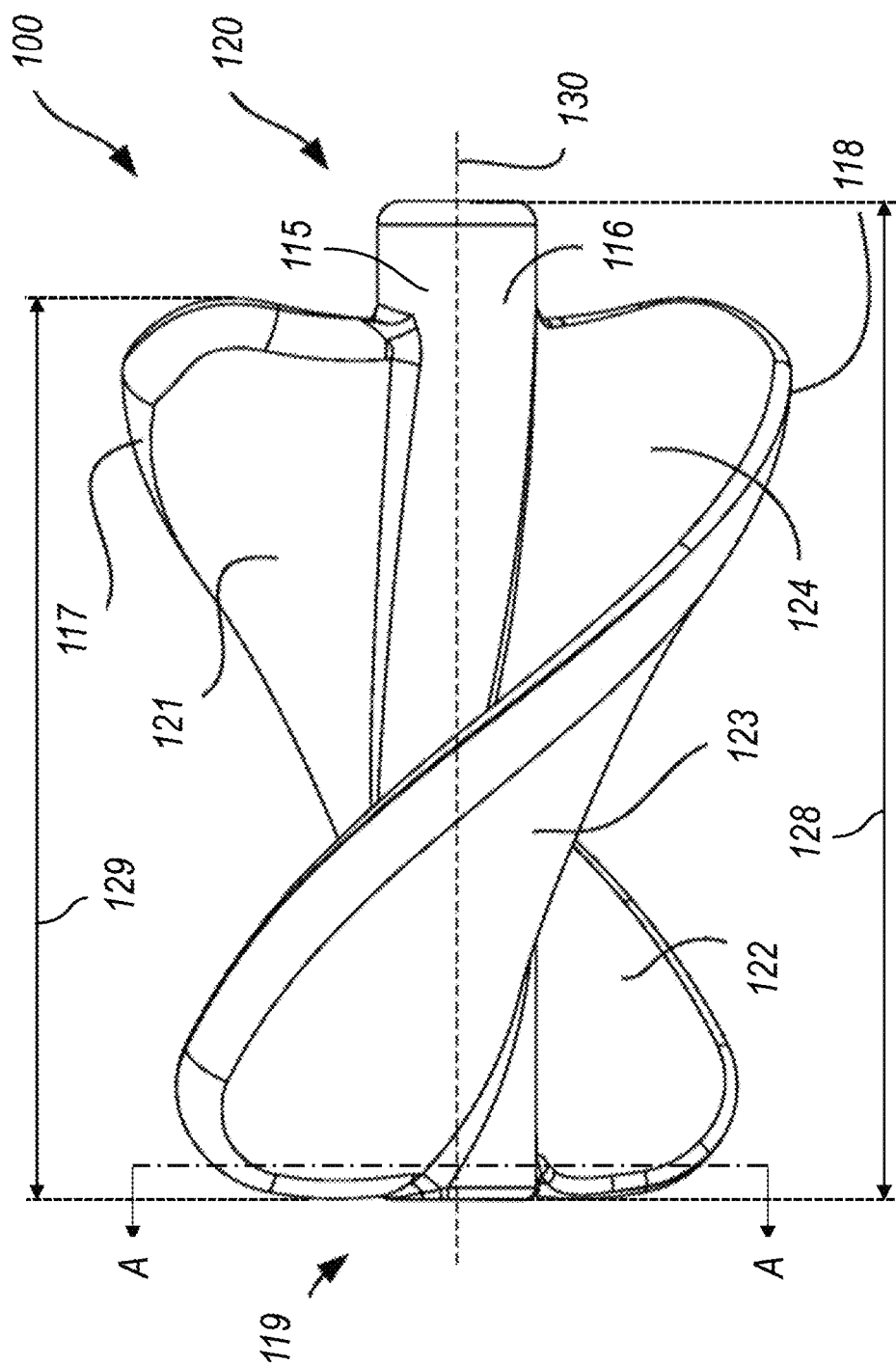
FIG. 2A is an illustration of a side view of a rotor in a running state.

A rotor may be provided. Referring to FIG. 2A, advantageously, the rotor 100 may include a hub 116 configured to rotate around a central axis 130. The rotor may include at least one rotor blade 117, 118 coupled to the hub and extending (radially) away from an outer surface 115 of the hub. The hub may have a distal end 119 and a proximal end 120, where rotation of the hub generates a flow of blood from, e.g., the distal end to the proximal end.

To reduce the shear stress on blood caused by the rotor, the rotor, and especially the blade(s), should have good quality surfaces. In some embodiments, the at least one blade 117, 118 may have a substantially smooth exterior surface, such as a first surface 121, 123 and a second surface 122, 124. In some embodiments, the at least one blade may have an exterior surface that is substantially free of an orange peel effect.

As used herein, "orange peel" or the "orange peel effect" refers to a certain kind of finish that may develop on surfaces. The non-smooth texture resembles the surface of the skin of an orange. Without being held to a particular theory, such orange peel effect is likely caused by shrinkage during curing. Further, such effects may be related to differences in the coefficient of linear expansion between materials that comprise the rotor or uneven control of temperatures during the processing of the component.

In some embodiments, the at least one blade 117, 118 may have an axial length 129 of 7-8 mm.

Figure 2B:
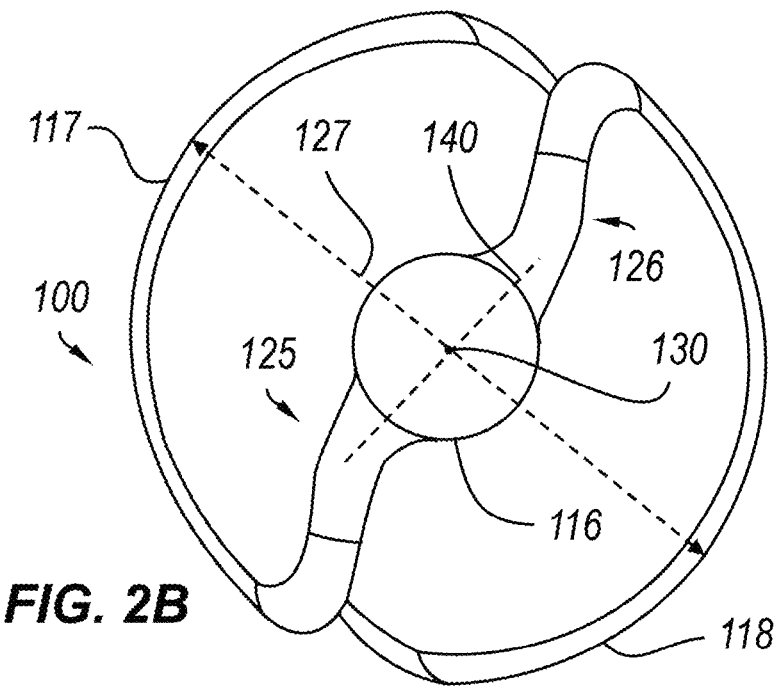
FIG. 2B is an illustration of an axial view of a rotor without a lumen.
Figure 4A:
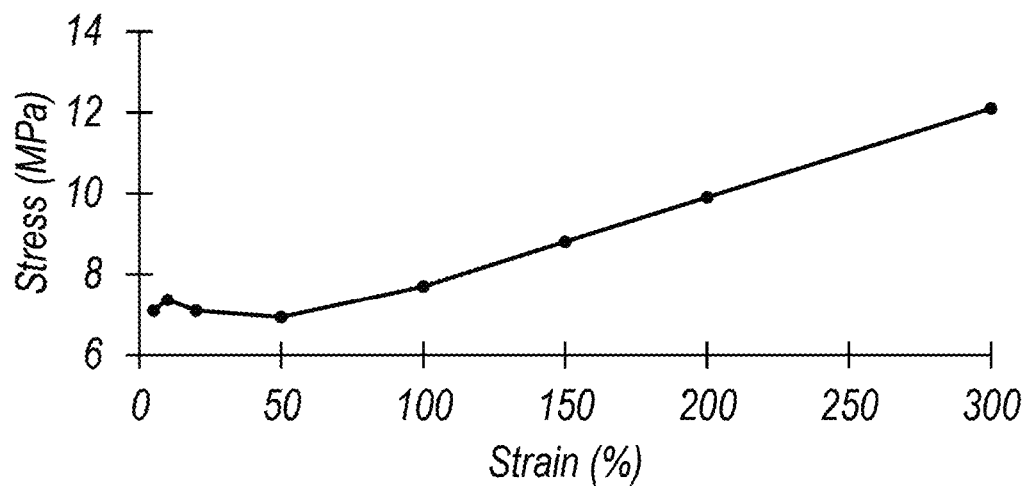
FIG. 4A is a graph showing a stress of a medical grade polymer at different strains.
Figure 4B:
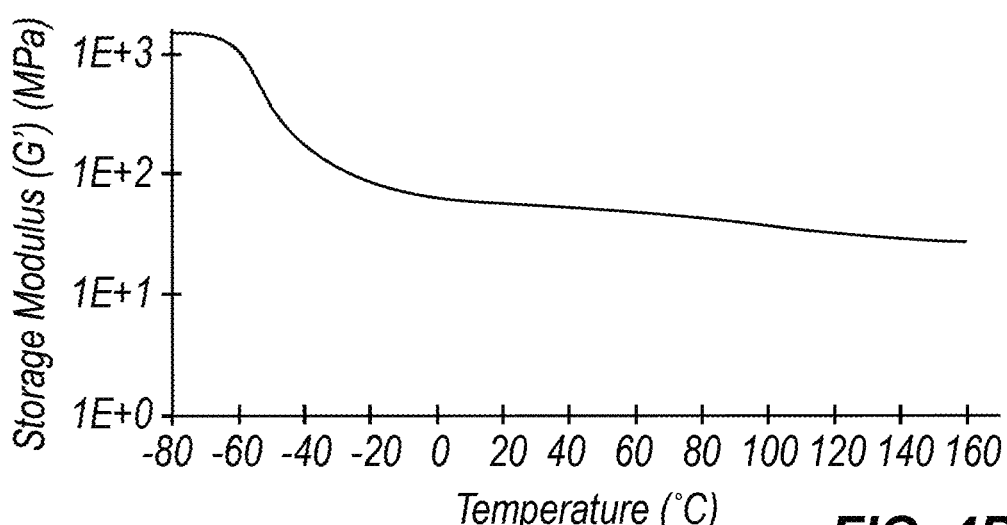
FIG. 4B is a graph showing a storage modulus (G') of a medical grade polymer during a temperature sweep.
Figure 4C:
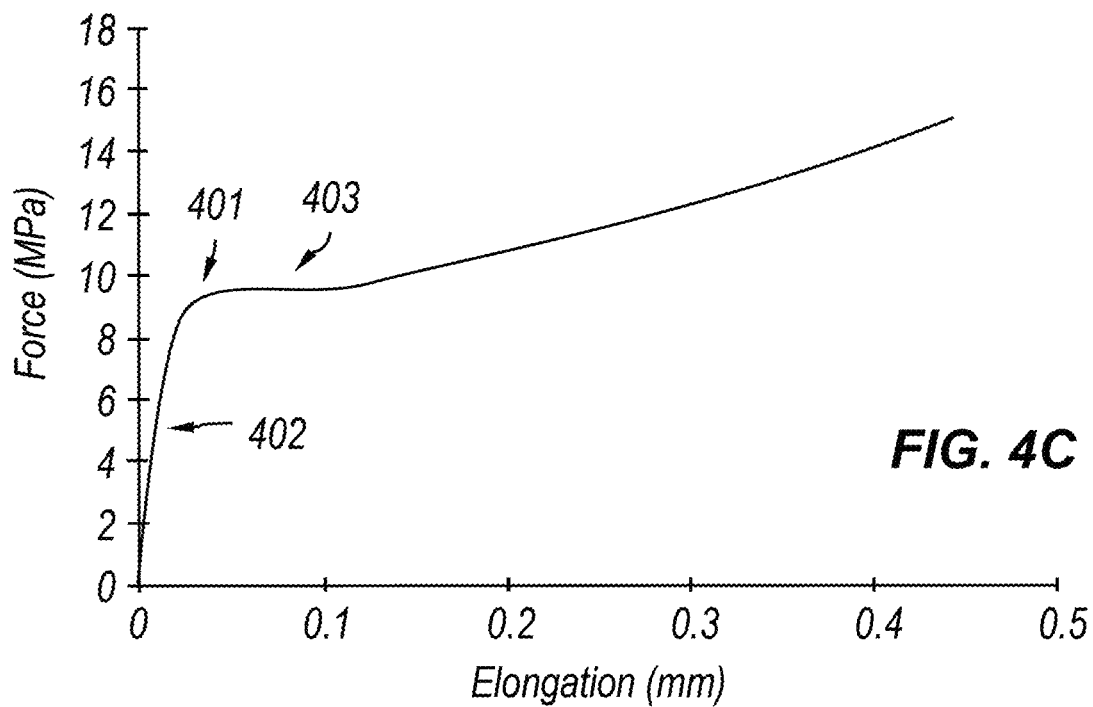
FIG. 4C is a graph showing an example force-elongation profile.

In some embodiments, the at least one rotor blade may be helically wound around the hub. As shown in FIG. 2B, in some embodiments, the at least one blade may be configured such that the rotor may have a maximum outer diameter 127 of 5-6 mm in the running state. In some embodiments, portions 125 and 126 are portions of blades 117 and 118, respectively, that are disposed directly adjacent to hub 116, and may be configured to extend away As shown, portions 125 and 126 extend along a radial axis 140 that orthogonally traverses the axis of rotation (e.g., central axis 130) of rotor 100 and extends through the center of hub 116. It is to be appreciated that, as seen in the cross-sectional views of rotor 5 (FIG. 2A), portions 125 and 126 (FIG. 2B) extend from the hub as illustrated in FIG. 4C (i.e., along radial axis 140) along at least a portion of a length of the hub (i.e., from distal end 119 some or all of the way to proximal end 120 of hub 116).

In some embodiments, the at least one rotor blade may have a constant helical pitch.

Figure 2C:
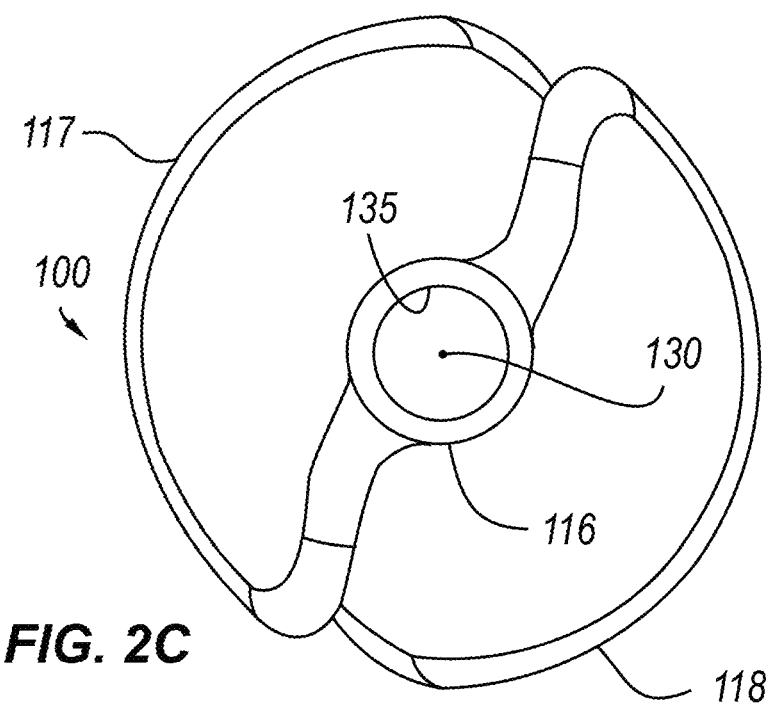
FIG. 2C is an illustration of an axial view of a rotor with a lumen.
Figure 2D:
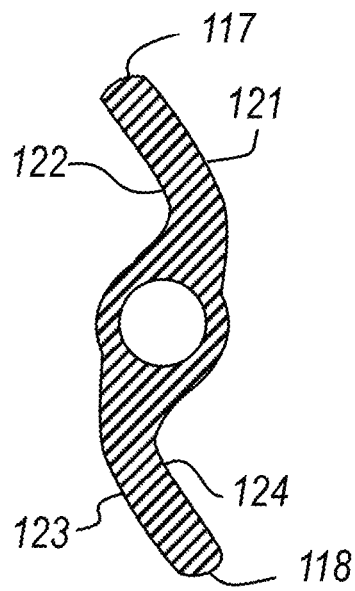
FIG. 2D is an illustration of a view of cross-section A as shown in FIG. 2A.

Referring to FIG. 2D, in some embodiments, the at least one rotor blades 117, 118 may each include a concave side 122, 124 and a convex side 121, 123. In some embodiments, a helical pitch of the at least one rotor blade may vary along a length of the hub. In some embodiments, the curvature of the outer portions of blades 117, 118 varies depending on the position along the length of the hub 116 from which the blades 117, 118 extend. In some embodiments, the inner curvature of the concave sides (here, proximal-facing sides 122, 124) of the blades, 117, 118 is tighter (i.e., at a smaller angle) than the curvature of the convex sides (here, distal-facing sides 121, 123) of the blades (which form a larger angle). Therefore, in some embodiments, the pitch of the each of the outer portions of the blades 117, 118 may vary along the length of the hub 116.

In some embodiments, the hub may have an axial length 128 of 9-11 mm. In some embodiments, such as that shown in FIG. 2B, the hub may be free of a lumen extending from a distal end to a proximal end. In some embodiments, such as that shown in FIG. 2C, the hub may have an inner surface 135 that defines a lumen extending from a distal end to a proximal end.

The rotor blade(s) may be configured to have a crimped state and a running state.

Figure 3:
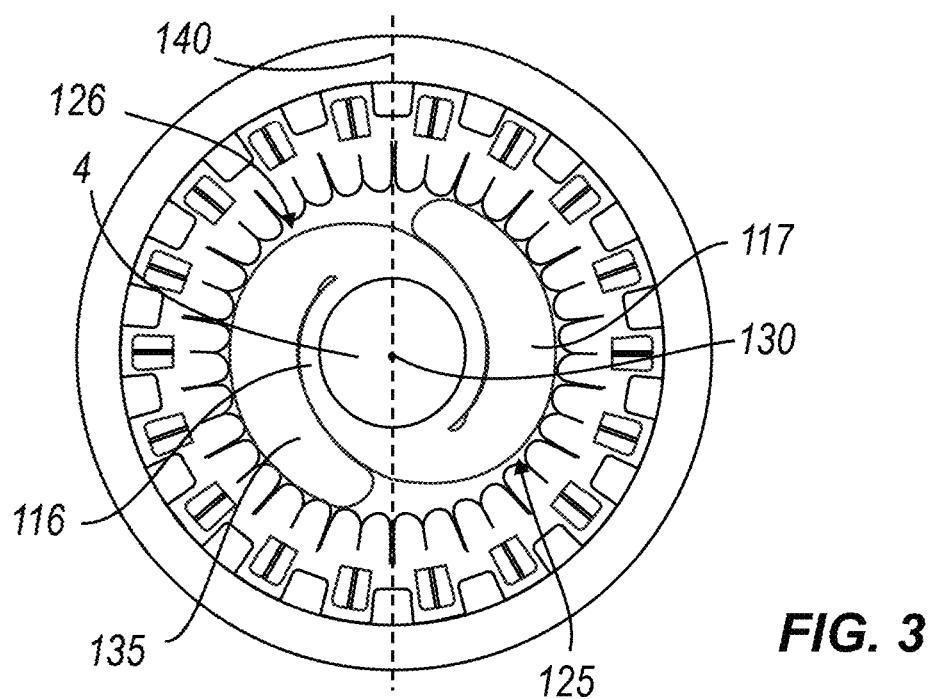
FIG. 3 is a cross-sectional view of a crimped rotor.

In some embodiments, the concave side may be laid against an exterior surface of the hub when in the crimped state. FIG. 3 shows an embodiment of a rotor in a compressed state. In the compressed state, rotor blades 117, 118 are folded onto hub 116, preferably without any folds having sharp angles, which may lead to kinking and possibly permanent deformation. As seen in FIG. 3, in the compressed/crimped state, portions 125, 126 of rotor blades 117, 118 with respect to radial axis 140 allows blades 117, 118 to wrap at least partially around hub 116, conforming to the hub curvature. Consequently, the sharp kinking that some conventional rotors experience in the compressed state is absent. Since blades 117, 118 lay relatively evenly against hub 116, the forces on blades 117, 118 when compressed are transferred into a torque on the outer diameter of the hub 116, thereby reducing or eliminating kinking in blades 117, 118 when compressed. The reduced stress on blades 117, 118 in the compressed state further allows blades 117, 118 to unfold to their natural position in the uncompressed/expanded ("running") state due to the reduced likelihood of permanent deformation of blades 117, 118 due to blade stress in the compressed state.

The rotor blade(s) be composed of a medical-grade material. The medical-grade material should be a biocompatible material. In some embodiments, the medical-grade material may include a thermoplastic polyurethane, or other thermoplastic elastomer such as a polyvinyl acetate, or a blend/combination thereof. In some embodiments, the medical-grade material may be a medical-grade polyurethane. In some embodiments, the medical-grade material may be a polyvinyl acetate. In some embodiments, the medical-grade material may be a single-component resin.

In some embodiments, the medical-grade material may be a resin, such as a polyurethane resin, having a first component and a second component. The first component may be a prepolymer of: (i) hexamethyl diisocyanate (HDI), methylene dicyclohexyl diisocyanate (H12MDI), and/or methylene diphenyl diisocyanate (MDI); (ii) polytetramethylene ether glycol (PTMEG) with a molecular weight of 500 g/mol-6,000 g/mol, or polypropylene glycol (PPG) (sometimes referred to herein as poly(propylene oxide) (PPO));

and (iii) optionally, polyesters like poly(caprolactone), polyethylene adipate, or polybutylene adipate, where the first component may have an average molecular weight of 10,000 g/mol-14,000 g/mol. The second component may be diethyltoluenediamine (DETDA) or 1,4 butane diol.

In some embodiments, the first component comprises HDI, PPG, and poly(caprolactone), and the second component is DETDA. In some embodiments, the first component comprises H12MDI, PPO, and poly(caprolactone), and the second component is DETDA. In some embodiments, the first component comprises H12MDI and/or MDI, PPO, and PTMEG, and the second component is 1,4 butane diol.

In some embodiments, the first component and second component may be present at a stoichiometric ratio. Advantageously, in some embodiments, the first component and second component may be present at a non-stoichiometric ratio. In some embodiments, the second component is used in an amount less than the stoichiometric ratio would dictate. In some embodiments, the second component may be present in an amount that is 60-90% of the amount required to meet the stoichiometric ratio. As a simple example of this, in some embodiments, the stoichiometric ratio of the components may be in the range of 1:0.65 to 1:1.35. Preferably, the range may be 1:0.75-1:1.25. In some preferred embodiments, the range may be 1:0.90-1:1.10. In some preferred embodiments, the range may be 1:1-1:1.20. In some preferred embodiments, the non-stoichiometric ratio used may be 1:0.95-1:1.05.

In some embodiments, the polyurethane may be composed of one or more soft segments and one or more hard segments, which may alternate (e.g., soft segment, hard segment, soft segment, hard segment, . . . ). This may include segmented polyurethanes, polyurethaneureas and polyureas.

The soft segment(s) may be di- or tri-functionally terminated telechelic soft segment oligomer(s). The soft segments may have molecular weights of at least 500 g/mol, 1000 g/mol, or 1500 g/mol up to 5000 g/mol, 5500 g/mol, or 6000 g/mol, including all combinations and subranges thereof. Non-limiting examples of soft segments include polyethers (such as poly(ethylene oxide) (PEO), poly(propylene oxide) (PPO), poly(tetramethylene oxide) (PTMO), or any blend thereof, including block copolymers of PEO and PPO).

The soft segments may include one or more halogen atoms, such as fluorine. For example, in some embodiments, the soft segments may include a fluorinated polyether oligomer.

The hard segments can be composed of diisocyanates such as those shown below in Table 1. In some embodiments, the one or more hard segments may be glassy. In some embodiments, the one or more hard segments may be semicrystalline. In some embodiments, the one or more hard segments may be crystalline.

Such segmented polyurethanes are generally known in the art, as are their manufacturing techniques. One example of such materials can be found in, e.g., U.S. Pat. No. 3,658,746 A, the contents of which are incorporated by reference herein in its entirety.

TABLE 1

| (List of Example Diisocyanates) | | |
|---|---|---|
| Diisocyanate | Abbreviation | Chemical structure |
| Hexamethylene | HDI | $OCN-(CH_2)_6-NCO$ |
| trans-1,4-cyclohexyl | CHDI | $OCN-\text{C}_6H_{10}-NCO$ |
| Bis(4-isocyanatocyclohexyl) | HMDI | $OCN-\text{C}_6H_{10}-CH_2-\text{C}_6H_{10}-NCO$ |
| Isophorone | IPDI | (structure with $H_3C$, $CH_2-NCO$, $OCN$, $CH_3$, $CH_3$) |
| 1,4-Phenylene | PPDI | $OCN-\text{C}_6H_4-NCO$ |
| 1,3-Phenylene | MPDI | (1,3-phenylene with $OCN$ and $NCO$) |
| 2,4-Tolylene | TDI | (2,4-tolylene with $OCN$, $NCO$, $CH_3$) |

TABLE 1-continued (List of Example Diisocyanates)

| Diisocyanate | Abbreviation | Chemical structure |
|---|---|---|
| 4,4'-Methylenediphenyl | MDI | 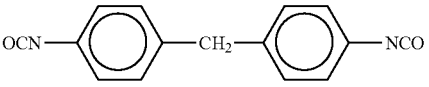 |

As will be understood, the polyurethane may include one or more chain extenders. As is understood in the art, chain extenders are used in polyurethane synthesis to, inter alia, increase the length of hard segments, tailoring the molecular weight of the polyurethane. Non-limiting examples of chain extenders include aromatic and aliphatic diamine chain extenders, such as 1,4-butanediol (BDO).

Figure 7:
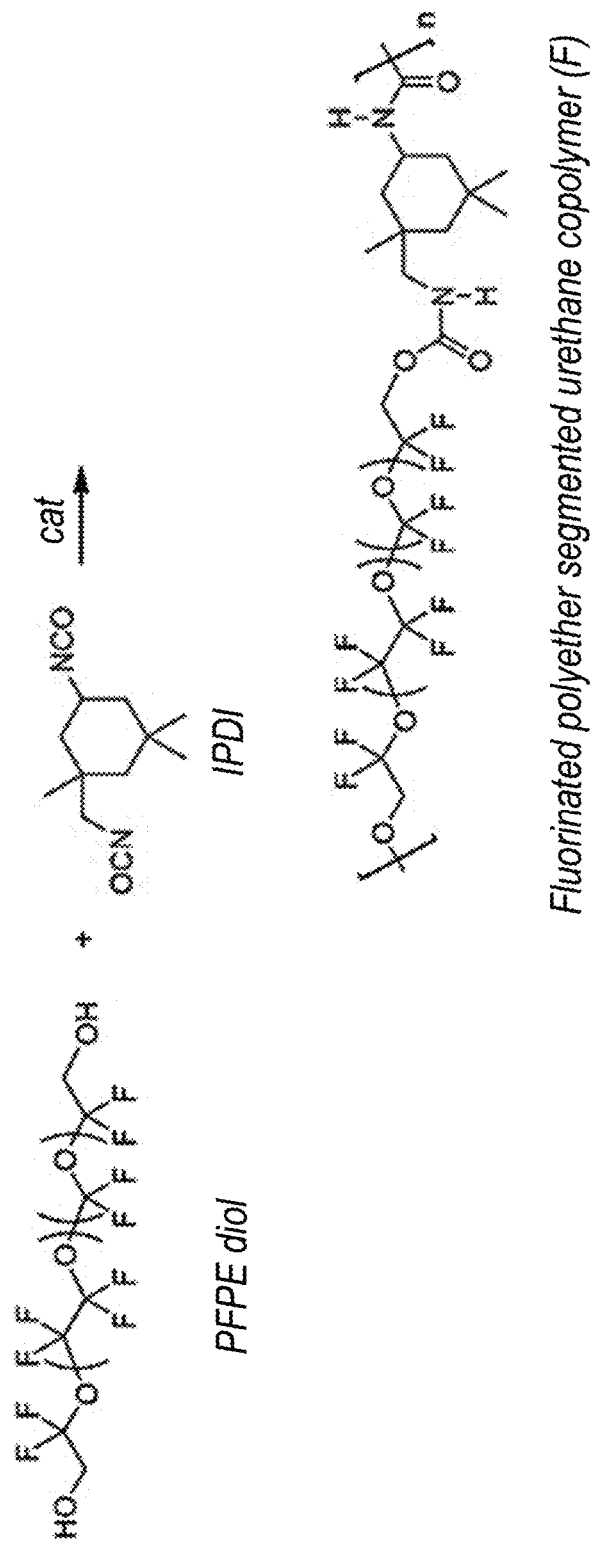
FIG. 7 is an illustration of a polymer synthesis reaction.

The polymers may be synthesized either in a one-shot polymerization method or via a "prepolymer method", which consists of two steps: 1) formation of an isocyanate terminated "prepolymer", followed by 2) a "chain extension" step where the prepolymer is reacted with a short organic diol or diamine to form the high molecular weight segmented polyurethane or segmented polyurethaneurea. One example of this is seen in FIG. 7.

In some embodiments, the medical-grade material may be a silicone-polycarbonate-urethane. Such materials are based on a soft polycarbonate urethane surrounded by long silicone chains (such as polydimethylsiloxane chains). The polycarbonate urethane may include one or more polycarbonate diols (which may have a molecular weight of, e.g., 500-6000 g/mol), and/or one or more aromatic or aliphatic isocynates (see Table 1). Such urethanes may be polymerized with a linear or branched diol chain extender such as 1,4-butanediol (BDO). As will be understood, different aromatic and aliphatic diamine chain extenders can be used. One example of a silicone-polycarbonate-urethane may be a polycarbonate(PC)-polydimethylsiloxane (PDMS)-MDI-BDO block copolymer. The relative ratios of the different components are adapted to achieve desired set of mechanical properties.

The siloxane may be a dihydroxyalkyl-terminated polydialkylsiloxane, such as a dihydroxypropyl-terminated polydimethylsiloxane.

The polysiloxane may have various reactive end groups. In some embodiments, the polysiloxane may include hydroxy groups. In some embodiments, the polysiloxane may include amino groups. In some embodiments, the polysiloxane may include isocyanate groups. In some embodiments, the polysiloxane may include hydroxy groups, amino groups, isocyanate groups, or any combination thereof.

The polysiloxane may have a molecular weight between about 500 Da and about 8000 Da. In some embodiment, the molecular weight is at least about 500 Da. In some embodiment, the molecular weight is at least about 1000 Da. In some embodiments, the molecular weight is at least about 2000 Da. In some embodiment, the molecular weight is at least about 3000 Da. In some embodiment, the molecular weight is no more than about 8000 Da. In some embodiment, the molecular weight is no more than about 7000 Da. In some embodiment, the molecular weight is no more than about 6000 Da. In some embodiment, the molecular weight is no more than about 5000 Da. In some embodiments, such urethane may include about 5% to about 30% by weight of the polysiloxane. In some embodiments, such urethane may include at least about 5% by weight of the polysiloxane. In some embodiments, such urethane may include at least about 10% by weight of the polysiloxane. In some embodiments, such urethane may include at least about 15% by weight of the polysiloxane. In some embodiments, such urethane may include at least about 20% by weight of the polysiloxane. In some embodiments, such urethane may include at least about 25% by weight of the polysiloxane. In some embodiments, such urethane may include no more than about 50% by weight of the polysiloxane. In some embodiments, such urethane may include no more than about 40% by weight of the polysiloxane. In some embodiments, such urethane may include no more than about 30% by weight of the polysiloxane.

Silicone-urethane polymers are generally known in the art, as are their manufacturing techniques. One example of such materials can be found in, e.g., U.S. Pat. No. 8,242,189 B2, the contents of which are incorporated by reference herein in its entirety.

In some embodiments, the medical-grade material may include a catalyst and/or an inhibitor. Any appropriate amount of catalyst and/or inhibitor may be used, depending on the chemistry involved. In some embodiments, the catalyst may be present in an amount of no more than 0.1% by weight of the medical grade material (including catalyst and/or inhibitor). In some embodiments, the inhibitor may be present in an amount of no more than 5% by weight of the medical grade material (including inhibitor and/or catalyst).

Conventionally, polymeric materials are often specified by CAS number, or a group (e.g., polypropylene, polystyrene, etc.). However, it will be understood by those of skill in the art that such approaches are insufficient by themselves. For example, unambiguous classification of polymers based on CAS number alone is insufficient, as the chain length, degree of branching, tacticity, etc., are not considered when a CAS number is assigned. While a polymer belonging to a group (e.g., polypropylene) is broadly defined by its assigned CAS number, specific properties will vary based on the macromolecular structure of the polymer (such as those features listed previously), manufacturing process, supplier of raw material, etc. Thus, it may be worth expanding upon features the medical grade material disclosed herein preferably incorporate.

The medical-grade material may be configured for casting or injection molding. For example, in some embodiments, the rotor may be formed by die-casting. In some embodiments, the rotor may be formed by injection molding. In some embodiments, the rotor may be formed by vacuum casting or vacuum socketing. Using materials that have low shrinkage is preferred. In some embodiments, the medical-grade material may be selected such that a dimensional molding shrinkage is less than 1% upon cooling to room temperature after forming the rotor.

In some embodiments, upon curing, the medical-grade material advantageously has a shore A hardness value of 90-100 as determined using DIN ISO 7619-1. In some embodiments, upon curing, the medical-grade material advantageously has a shore B hardness value of 35-55 as determined using DIN ISO 7619-1. In some embodiments, upon curing, the medical-grade material advantageously has a Young's modulus of 60 MPa-250 MPa as determined using ISO 527.

In some embodiments, the rotor blade(s) may be configured to be capable of being exposed to two different use conditions for extended periods (30 minutes or more) without substantial permanent deformation (e.g., 5% or less of unrecoverable deformation). Specifically, in some embodiments, the rotor blade(s) may be configured to be exposed to strains of up to about 160% in a dry environment at temperatures of 20-25° C. in a crimped state. In some embodiments, the rotor blade(s) may be configured to be exposed to strains of up to 10% in a wet environment (e.g., exposed to blood) at temperatures of 36-42° C. while in a running (expanded) state. In some embodiments, the rotor blade(s) may be configured to be exposed to strains of up to 10% in a wet environment (e.g., exposed to blood) at temperatures of 36-40° C. while in a running (expanded) state. In some embodiments, the rotor blade(s) may be configured to be exposed to strains of up to 10% in a wet environment (e.g., exposed to blood) at temperatures of 36-38° C. while in a running (expanded) state.

In some embodiments, the medical-grade material may preferably have a tensile strength of 15 MPa-25 MPa, and an elongation at break of 500%-600% as determined using DIN 53504. For example, one thermoplastic polyurethane as disclosed herein had a measured tensile strength of 20 MPa, and an elongation at break of 540%. In some embodiments, the material may have an elongation at break of 150%-600% as determined using DIN 53504.

In some embodiments, the medical-grade material may preferably be selected such that the stresses measured across a range of strains, are relatively constant. For example, as shown in FIG. 4A, in some embodiments, a stress of the medical-grade material at 5% strain, a stress at 10% strain, a stress at 20% strain, and a stress at 50% strain may, across the four stresses, have a range of no more than 0.5 MPa, as determined using DIN 53504.

In some embodiments, the medical-grade material may have a storage modulus exhibiting a rubbery plateau at temperatures from no more than 0° C. to no less than 150° C. In some embodiments, the medical-grade material may have a storage modulus of 50-100 MPa at 0° C. As example of this can be seen in, e.g., FIG. 4B.

Figure 4D:
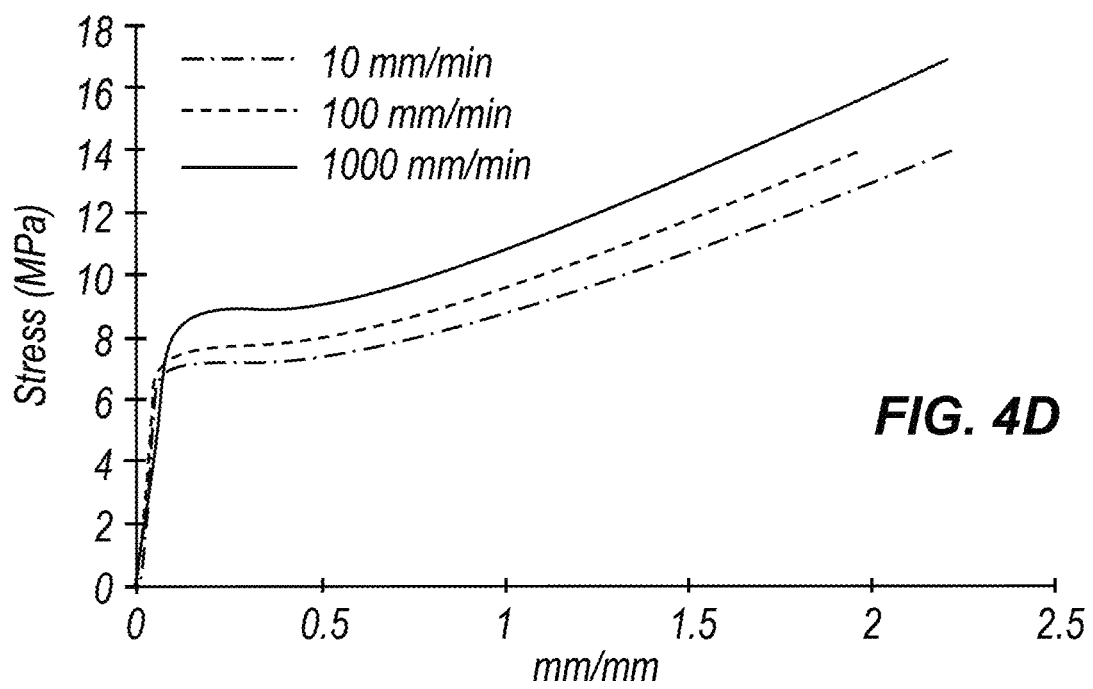
FIG. 4D is a graph showing an engineering stress-strain curve of a medical grade polymer.

Preferably, the force required to transition from running state to crimped state (e.g., when a clinician wishes to remove the pump from a patient) is not excessive. To achieve this, in some embodiments, the medical-grade material may be selected such that a force-elongation profile of the medical-grade material exhibits a region with a first slope below a deformation threshold and a plateau region above the deformation threshold. FIG. 4C is an example of a force-elongation test, showing the first region 402 with a first slope, that is below the deformation threshold 401, and the plateau region 403 that is above the deformation threshold. These same basic features can also be seen when the force-elongation curves are converted to engineering stress-strain curves. This can be seen in, e.g., FIG. 4D, where a similar first region and plateau region can be seen. In some embodiments, values of force in the plateau region may be 9-11 N.

Depending on various factors, such as the shape of the rotor and blades, and what degree of crimping is required, the amount of elongation required in use may exceed 100%, 150%, 200%, or 300%. In some embodiments, the medical-grade material may be configured to survive elongations greater than 100% without rupturing. In some embodiments, the medical-grade material may be configured to survive elongations greater than 150% without rupturing. In some embodiments, the medical-grade material may be configured to survive elongations greater than 200% without rupturing. In some embodiments, the medical-grade material may be configured to survive elongations greater than 300% without rupturing.

Further, to avoid degradation of performance over time, the rotor it should be able to be exposed to certain elongations without large amounts of non-recoverable plastic deformation. In some embodiments, the medical-grade material may be configured such that, when exposed to an elongation of 100% for at least 15 minutes, the material exhibits less than 5% non-recoverable plastic deformation.

For rotors intended to be used as part of a medical device, the rotors should be able to be sterilized. Thus, in some embodiments, the medical-grade material may be a sterilizable material. In some embodiments, the medical-grade material may be ethylene oxide (ETO) sterilizable. In preferred embodiments, the medical-grade material may be ETO sterilizable but not autoclave sterilizable and/or gamma radiation sterilizable. For example, in some embodiments, the heat and pressure used for the autoclave may negatively impact the medical-grade material, and thus, an autoclave may not be used. Preferably, the medical-grade material does not absorb any detectable amount of ETO.

In some embodiments, a pump may be provided. Referring to FIG. 1, in some embodiments, the pump may include a pump housing 2 that is expandable and compressible. In some embodiments, the pump housing may include a structural layer, which may comprise, e.g., a plurality of struts forming a cage or mesh. The struts may comprise, e.g., nitinol. The pump housing may include additional layers, such as an inner and/or outer layer disposed on an inner surface or outer surface, respectively, of the struts or other structural layer. This may include filling spaces between struts to form a sealed area, where fluid cannot travel between the inside and outside of the housing through the sealed area. The pump may include a rotor 100 as disclosed herein, the rotor being disposed in the pump housing.

In some embodiments, the pump may include a drive shaft 4 operably coupled to the rotor. In some embodiments, the drive shaft may be a flexible drive shaft. In some embodiments, the drive shaft may be a metallic drive shaft. In some embodiments, the drive shaft may be composed of a single filament. In some embodiments, the drive shaft may be composed of multiple filaments, which may be combined in a single layer or in multiple layers. In some embodiments, the driveshaft may be hollow (e.g., a lumen may extend from a distal end to a proximal end of the drive shaft). In some embodiments, the rotor may be adhered to the metallic drive shaft.

Figure 5A:
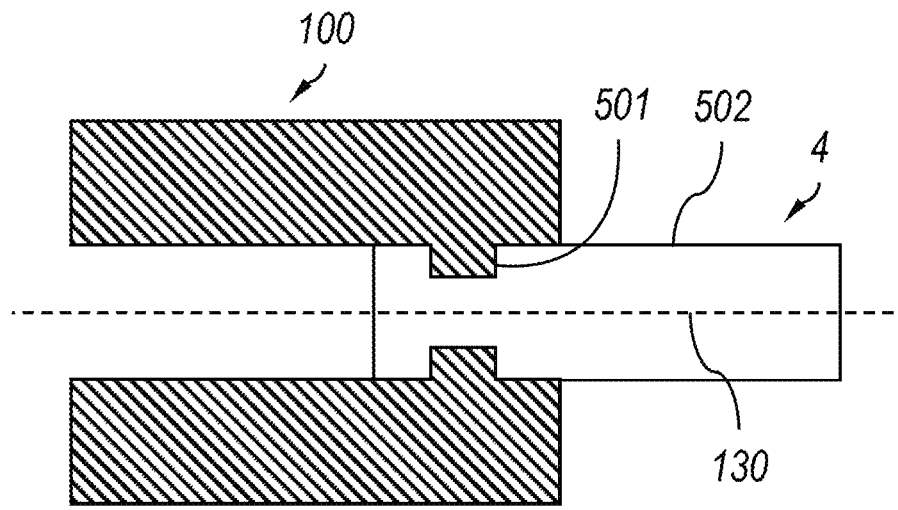
FIGS. 5A and 5B are simplified cross-sectional illustrations showing structural elements for coupling a rotor to a drive shaft.
Figure 5B:
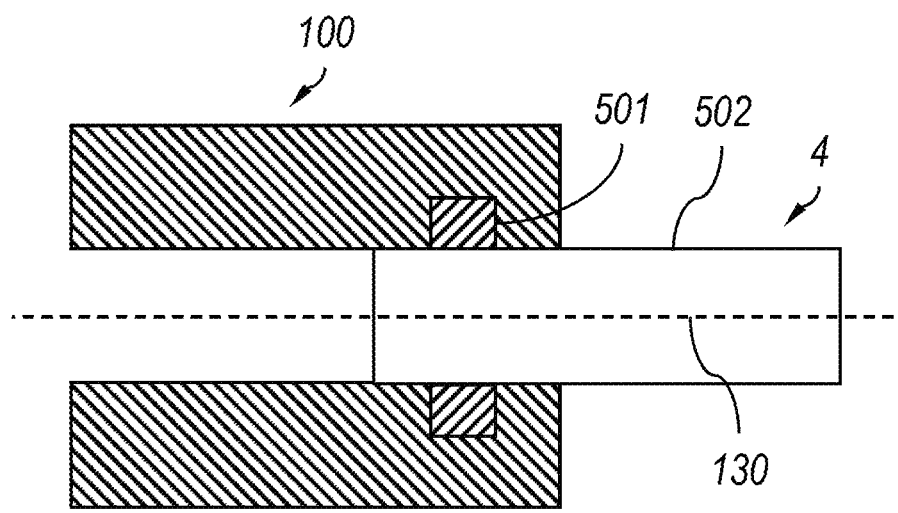

In some embodiments, the metallic drive shaft may include at least one structure 501 extending in a radial direction (such as radially inward (FIG. 5A) and/or radially outward (FIG. 5B) from an outer surface 502, relative to the central axis 130 of the drive shaft, where the at least one structure is configured to interact with the rotor, to prevent slippage (such as movement axially and/or movement circumferentially relative to the drive shaft). In some embodiments, the metallic drive shaft may be free of structures extending radially outward from the drive shaft that interact with the rotor. In some embodiments, at least a portion of the metallic drive shaft may have been surface treated. Such surface treatments may include, e.g., laser-blasting (such as laser bead blasting), sand-blasting, transfer-blasting, plasma treating. The surface treatment may include creating sideholes (i.e., in combination with a hollow drive shaft). For example, in some embodiments, a portion of the drive shaft may be exposed to a UV/ozone treatment to improve adhesion of the medical-grade material to the drive shaft.

Referring to FIG. 1, in some embodiments, the pump may include a motor 6 operably coupled to a proximal end of the drive shaft. In some embodiments, the pump may include a catheter 3 having a proximal end and a distal end, the distal end operably coupled to a proximal end of the pump housing.

Figure 6:
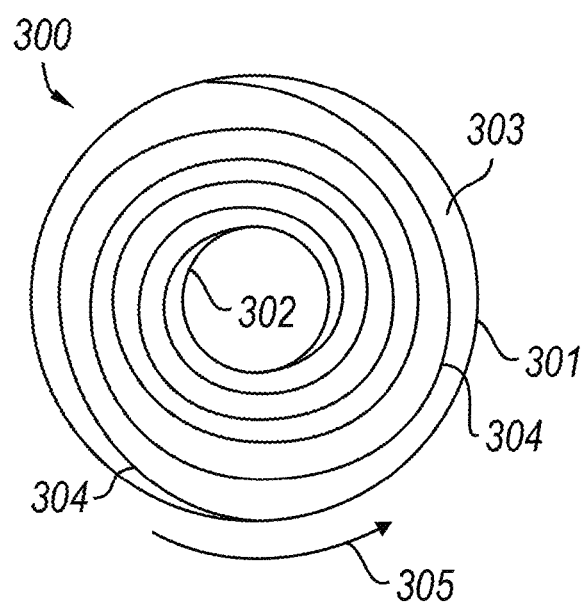
FIG. 6 is an illustration of a bearing surface in plan view according to one embodiment.

In some embodiments, the drive shaft may be disposed in a lumen extending from the proximal end to the distal end of the catheter. The lumen may include bearings (not shown). Various bearings may be used. In some embodiments, a spiral bearing may be used. Referring to FIG. 6, a spiral bearing 300 may have an outer surface 301 (facing radially outward from a central axis of rotation) and in inner surface 302 (facing radially inward towards a central axis of rotation). The spiral bearing may be a so-called spiral groove bearing, which is preferably formed on the moving surface of the bearing gap, i.e., accordingly on the surface 303 of bearing. In this case, several grooves 304 are spirally disposed in the surface 303. The grooves are indicated only schematically in FIG. 6. When the bearing rotates in the direction 305 indicated by the arrow, a lubricating film may be conveyed radially inward along the grooves 304 and builds up a pressure there which in turn ensures that the surfaces forming the bearing gap (e.g., an axial gap, such as between the surface 303 and another surface opposing it) are kept at a distance apart.

In some embodiments, the pump housing may be configured to be inserted into a blood vessel of a patient. In some embodiments, the pump housing may be configured to be inserted into a ventricle of a heart of a patient.

In some embodiments, a system may be provided. The system may include a pump 1 as disclosed herein. A controller 31 may be operably coupled to the pump.

In some embodiments, a kit may be provided. The kit may include a pump 1 as disclosed herein, and a controller 31 that may be configured to be operably coupled to the pump.

Embodiments of the present disclosure are described in detail with reference to the figures wherein like reference numerals identify similar or identical elements. It is to be understood that the disclosed embodiments are merely examples of the disclosure, which may be embodied in various forms. Well known functions or constructions are not described in detail to avoid obscuring the present disclosure in unnecessary detail. Therefore, specific structural and functional details disclosed herein are not to be interpreted as limiting, but merely as a basis for the claims and as a representative basis for teaching one skilled in the art to variously employ the present disclosure in virtually any appropriately detailed structure.

Those skilled in the art will recognize or be able to ascertain using no more than routine experimentation many equivalents to the specific embodiments of the invention described herein. Such equivalents are intended to be encompassed by the following claims.

What is claimed is:

1. A rotor comprising:
   a hub configured to rotate around a central axis; and
   at least one rotor blade coupled to the hub and extending away from an outer surface of the hub, the at least one rotor blade comprising a medical-grade material, the at least one rotor blade configured to have a crimped state and a running state;
   wherein the medical-grade material is configured for casting or injection molding, and upon curing, the medical-grade material having a shore A hardness value of 90-100 or shore B hardness value of 35-55 as determined using DIN ISO 7619-1 and a Young's modulus of 60 Mpa-250 MPa as determined used ISO 527;
   wherein in the crimped state, the at least one rotor blade is compressed and exposed to strains of up to about 160% in a dry environment at temperatures of 20-25° C.; and
   wherein in the running state, the at least one rotor blade is expanded and exposed to strains of up to 10% in a wet environment at temperatures of 36-42° C.

2. The rotor according to claim 1, wherein the medical-grade material has a tensile strength of 15 Mpa-25 MPa, and an elongation at break of 500%-600% as determined using DIN 53504.

3. The rotor according to claim 2, wherein the medical-grade material has a stress at 5% strain, a stress at 10% strain, a stress at 20% strain, and a stress at 50% strain have a range of no more than 0.5 MPa, as determined using DIN 53504.

4. The rotor according to claim 1, wherein the medical-grade material has a storage modulus exhibiting a rubbery plateau at temperatures from no more than 0° C. to no less than 150° C.

5. The rotor according to claim 4, wherein the medical-grade material has a storage modulus of 50-100 MPa at 0° C.

6. The rotor according to claim 1, wherein the medical-grade material is a resin having a first component and a second component;
   wherein the first component is a prepolymer including:
      hexamethyl diisocyanate (HDI), methylene dicyclohexyl diisocyanate (H12MDI), and/or methylene diphenyl diisocyanate (MDI); and
      polytetramethylene ether glycol (PTMEG) with a molecular weight of 500 g/mol-6,000 g/mol, or polypropylene glycol (PPG);
      the first component having an average molecular weight of 10,000 g/mol-14,000 g/mol; and
   wherein the second component being diethyltoluenediamine (DETDA) or 1,4 butane diol.

7. The rotor according to claim 6, wherein the first component and second component are present at a stoichiometric ratio.

8. The rotor according to claim 6, wherein the first component and second component are present at a non-stoichiometric ratio.

9. The rotor according to claim 1, wherein the medical-grade material is a resin having one or more soft segments and one or more hard segments.

10. The rotor according to claim 9, wherein the one or more soft segments includes a di- or tri-functionally terminated telechelic soft segment oligomer, and the one or more hard segments includes a diisocyanate.

11. The rotor according to claim 10, wherein the medical-grade material further comprises one or more chain extenders.

12. The rotor according to claim 1, wherein the medical-grade material is a silicone-polycarbonate-urethane that includes polydimethylsiloxane (PDMS) and one or more chain extenders.

13. The rotor according to claim 1, wherein the medical-grade material is a single-component resin.

14. The rotor according to claim 1, wherein the medical-grade material is selected such that a force-elongation profile of the medical-grade material exhibits a region with a first slope below a deformation threshold and a plateau region above the deformation threshold.

15. The rotor according to claim 1, wherein the medical-grade material includes a catalyst and/or an inhibitor.

16. The rotor according to claim 1, wherein the hub and at least one rotor blade are cast or molded from the medical-grade material.

17. A pump comprising:
a pump housing that is expandable and compressible; and
a rotor according to claim 1, the rotor disposed in the pump housing.

18. A system comprising:
the pump according to claim 17; and
a controller operably coupled to the pump.

19. A kit comprising:
the pump according to claim 17; and
a controller configured to be operably coupled to the pump.

20. The rotor according to claim 6, wherein the first component further comprises a polyester.

* * * * *